US005523484A

United States Patent [19]

Wilson et al.

[11] Patent Number: 5,523,484

[45] Date of Patent: Jun. 4, 1996

[54] BIS AND TRIS N-(CARBONYL, CARBONIMIDOYL, CARBONOTHIOYL) SULFONAMIDE CHARGE CONTROL AGENTS, TONERS AND DEVELOPERS

[75] Inventors: John C. Wilson; Peter S. Alexandrovich, both of Rochester, N.Y.

[73] Assignee: Eastman Kodak Company, Rochester, N.Y.

[21] Appl. No.: 316,006

[22] Filed: Sep. 30, 1994

Related U.S. Application Data

[62] Division of Ser. No. 171,784, Dec. 22, 1993, Pat. No. 5,385,800.

[51] Int. Cl.$^6$ .................................................. C07C 311/51

[52] U.S. Cl. .............................. 564/82; 564/83; 430/110; 430/126

[58] Field of Search .................................... 430/110, 126; 564/82, 83

[56] References Cited

U.S. PATENT DOCUMENTS

| | | | |
|---|---|---|---|
| Re. 31,072 | 11/1982 | Jadwin et al. | 430/49 |
| 3,498,780 | 3/1970 | Soper | 71/103 |
| 3,547,822 | 12/1970 | Miller | 430/106.6 |
| 3,577,345 | 5/1971 | Jacknow et al. | 430/110 |
| 3,632,512 | 1/1972 | Miller | 430/137 |
| 3,795,618 | 3/1974 | Kasper | 430/108 |
| 3,850,663 | 11/1974 | Hagenbach | 430/108 |
| 3,893,934 | 7/1975 | Braun et al. | 430/110 |
| 3,898,170 | 8/1975 | Kasper | 470/108 |
| 3,970,571 | 7/1976 | Olson et al. | 252/62.1 P |
| 4,002,776 | 1/1977 | Braun et al. | 430/110 |
| 4,042,518 | 8/1977 | Jones | 430/108 |
| 4,076,857 | 2/1978 | Kasper et al. | 430/103 |
| 4,160,644 | 7/1979 | Ryan | 252/408 |
| 4,394,430 | 7/1983 | Jadwin et al. | 430/110 |
| 4,414,152 | 11/1983 | Santilli et al. | 430/114 |
| 4,416,965 | 11/1983 | Sandhu et al. | 430/109 |
| 4,454,060 | 10/1985 | Arnou | 252/547 |
| 4,464,452 | 8/1984 | Gruber et al. | 430/110 |
| 4,478,925 | 10/1984 | Miskinis | 430/137 |
| 4,480,021 | 10/1984 | Lu et al. | 430/106.6 |
| 4,517,272 | 5/1985 | Jadwin et al. | 430/110 |
| 4,546,060 | 10/1985 | Miskins et al. | 430/108 |
| 4,684,596 | 8/1987 | Bonser et al. | 430/110 |
| 4,726,994 | 2/1988 | Yoerger | 430/137 |
| 4,758,491 | 7/1988 | Alexandrovich et al. | 430/110 |
| 5,157,156 | 10/1992 | Giordano et al. | 568/64 |
| 5,186,736 | 2/1993 | Ort et al. | 564/225 |
| 5,192,637 | 3/1993 | Salto et al. | 430/109 |

FOREIGN PATENT DOCUMENTS 0902881 8/1962 United Kingdom .

*Primary Examiner*—Peter O'Sullivan

*Attorney, Agent, or Firm*—Robert Luke Walker; Anne B. Kiernan

[57] ABSTRACT

An electrophotographic toner having polymeric binder and a charge control agent selected from the group consisting of sulfonamides having the general structure:

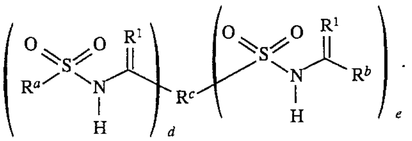

Each $R^1$ is independently O, S, N-H, N-$R^z$, or N-L-$R^z$; where L is a linking group selected from:

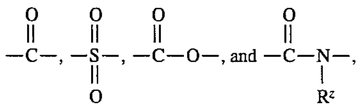

and $R^z$ is independently selected from the group consisting of alkyl having from 1 to 20 carbons, cycloalkyl having from 3 to 18 carbons, and aromatic and heteroaromatic ring systems having a solitary ring or 2 to 3 linked or fused rings. $R^a$, $R^b$, and $R^c$ are each independently a ring system of a single ring or 2 or 3 fused or linked rings, said ring system having from 3 to 34 carbons, including substituent carbons. d is an integer from 0 to 3. e is an integer from 0 to 3. The sum of d+e is 2 or 3.

19 Claims, No Drawings

BIS AND TRIS N-(CARBONYL, CARBONIMIDOYL, CARBONOTHIOYL) SULFONAMIDE CHARGE CONTROL AGENTS, TONERS AND DEVELOPERS

This application is a division of Ser. No. 171,784, filed 22 Dec. 1993, now U.S. Pat. No. 5,385,800.

FIELD OF THE INVENTION

The invention relates to electrographic materials, particularly charge control agents, and toners and developers incorporating those agents. This invention more particularly relates to bis and tris N-(carbonyl, carbonimidoyl, carbonothioyl)sulfonamide charge control agents and toners and developers including those agents.

BACKGROUND OF THE INVENTION

In electrography, image charge patterns are formed on a support and are developed by treatment with an electrographic developer containing marking particles which are attracted to the charge patterns. These particles are called toner particles or, collectively, toner. Two major types of developers, dry and liquid, are employed in the development of the charge patterns.

In electrostatography, the image charge pattern, also referred to as an electrostatic latent image, is formed on an insulative surface of an electrostatographic element by any of a variety of methods. For example, the electrostatic latent image may be formed electrophotographically, by imagewise photo-induced dissipation of the strength of portions of an electrostatic field of uniform strength previously formed on the surface of an electrophotographic element comprising a photoconductive layer and an electrically conductive substrate. Alternatively, the electrostatic latent image may be formed by direct electrical formation of an electrostatic field pattern on a surface of a dielectric material.

One well-known type of electrostatographic developer comprises a dry mixture of toner particles and carrier particles. Developers of this type are employed in cascade and magnetic brush electrostatographic development processes. The toner particles and carrier particles differ triboelectrically, such that during mixing to form the developer, the toner particles acquire a charge of one polarity and the carrier particles acquire a charge of the opposite polarity. The opposite charges cause the toner particles to cling to the carrier particles. During development, the electrostatic forces of the latent image, sometimes in combination with an additional applied field, attract the toner particles. The toner particles are pulled away from the carrier particles and become electrostatically attached, in imagewise relation, to the latent image bearing surface. The resultant toner image can then be fixed, by application of heat or other known methods, depending upon the nature of the toner image and the surface, or can be transferred to another surface and then fixed.

Toner particles often include charge control agents, which, desirably, provide high uniform net electrical charge to toner particles without reducing the adhesion of the toner to paper or other medium. Many types of positive charge control agents, materials which impart a positive charge to toner particles in a developer, have been used and are described in the published patent literature. In contrast, few negative charge control agents, materials which impart a negative charge to toner particles in a developer, are known.

Prior negative charge control agents have a variety of shortcomings. Many charge control agents are dark colored and cannot be readily used with pigmented toners, such as cyan, magenta, yellow, red, blue, and green. Some are highly toxic or produce highly toxic by-products. Some are highly sensitive to environmental conditions such as humidity. Some exhibit high throw-off or adverse triboelectric properties in some uses. Use of charge control agents requires a balancing of shortcomings and desired characteristics to meet a particular situation. There is thus a continuing need for negative charge control agents which have improved properties.

U.S. Pat. No. 4,480,021 teaches the use as negative charge control agents of sulfonamides and sulfones having the formula: $R_1—SO_2—R_2$ or $R_3—SO_2—NH—R_4$, in which $R_1$ is alkyl having from about 6 to about 22 carbons or aryl, $R_2$ is aryl having from about 6 to about 18 carbons, $R_3$ is aryl or alkyl group, and $R_4$ is alkyl, independent from $R_3$ having from about 6 to 22 carbons or aryl. Specific examples of aryl alkyl sulfonamides were named: para-tolyl stearyl sulfonamide, para-tolyl cetyl sulfonamide, para-xylyl stearyl sulfonamide, para-tolyl myristyl sulfonamide, and isopropyl biphenyl stearyl sulfonamide.

U.S. Pat. No. 4,464,452 teaches toner compositions including a negative charge control agent having the general structure:

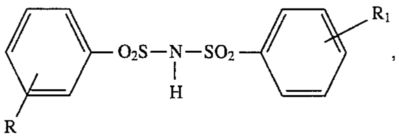

(1)

in which R and $R_1$ are selected from H, alkyl, halo, nitro, "and the like". This patent also teaches as specific examples of negative charge control agents: di-tolyl sulfonimide, phenyl tolyl sulfonimide, diphenyl sulfonimide, di-1-naphthyl sulfonimide, hexadecyl tolyl sulfonimide, methyl tolyl sulfonimide, and dihexadecyl sulfonimide.

U.S. Pat. No. 3,577,345 teaches toners and developers including a material having the general structure:

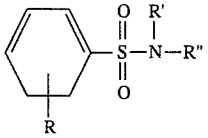

(2)

in which R is selected from H, Cl, Br, aryl, alkyl having from 1 to 6 carbons; R' and R" are selected from H, aryl having from 1 to 12 carbons and alkyl having from 1 to 12 carbons and chlorinated Ph-$(Ph)_n$-Ph (n=0–3). This material is not used as a charge control agent, but rather as an additive for modifying toner melt and viscosity. Similar melt and viscosity modifying additives are taught in U.S. Pat. Nos. 3,893,934 and 4,002,776. Those additives have the general structure:

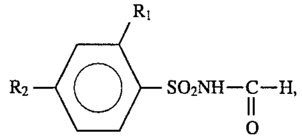

(3)

in which one of $R_1$ and $R_2$ is $CH_3$ and the other is H. These three patents do not teach or suggest whether these materials are capable of functioning as charge control agents for modification of charge. Charge control agents are commonly used in the range of about 0.5 to 3.0 weight percent. The melt and viscosity additives, in these patents have concentrations in toners in the range of about 10 to 40 weight percent.

U.S. Pat. No. 5,186,736 to Ong et al teaches toners having charge control additives having the general structure

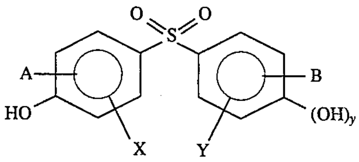

where A and B are independently selected from hydrogen, alkyl, alkoxy, carboxy, nitro, and halogen and X and Y are independently selected from hydrogen, hydroxy, alkyl, alkoxy, carboxy, nitro, and halogen and y is 0 or 1.

U.S. Pat. No. 5,186,736 to Ort et al teaches heterocyclic N-acylsulfonamide herbicides or growth regulators having the general structure:

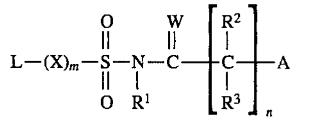

where $R^1$ is H or an aliphatic radical; $R^2$ and $R^3$ are H, alkyl or phenyl; W is O, S, $NR^4$ or $NOR^4$; X is $CHR^2$, O or $NR^4$; L is a (substituted) phenyl, naphthyl, or monocyclic heteroaryl radical; A is a (substituted) pyrimidyl, triazinyl, triazolyl or bicyclic heteroaryl radical; $R^4$ is H, $C_1$-$C_3$-alkyl, $C_1$-$C_3$-haloalkyl, or phenyl; and m and n are 0 or 1.

SUMMARY OF THE INVENTION

The invention, in its broader aspects, provides an electrophotographic toner comprising polymeric binder and a charge control agent selected from the group consisting of sulfonamides having the general structure:

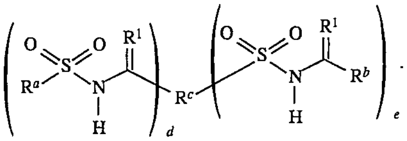

Each $R^1$ is independently O, S, N-H, N-$R^z$, or N-L-$R^z$; where L is a linking group selected from:

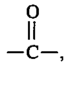, 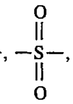, 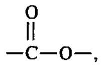, and 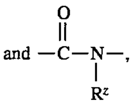, and $R^z$ is independently selected from the group consisting of alkyl having from 1 to 20 carbons, cycloalkyl having from 3 to 18 carbons, and aromatic and heteroaromatic ring systems having a solitary ring or 2 to 3 linked or fused rings. $R^a$, $R^b$, and $R^c$ are each independently a ring system of a single ring or 2 or 3 fused or linked rings, said ring system having from 3 to 34 carbons, including substituent carbons. d is an integer from 0 to 3. e is an integer from 0 to 3. The sum of d+e is 2 or 3.

It is an advantageous effect of at least some of the embodiments of the invention that negatively charging toners can be provided which have favorable charging characteristics.

DESCRIPTION OF PARTICULAR EMBODIMENTS

The term "particle size" used herein, or the term "size", or "sized" as employed herein in reference to the term "particles", means the median volume weighted diameter as measured by conventional diameter measuring devices, such as a Coulter Multisizer, sold by Coulter, Inc of Hialeah, Fla. Median volume weighted diameter is the diameter of an equivalent weight spherical particle which represents the median for a sample; that is, half of the mass of the sample is composed of smaller particles, and half of the mass of the sample is composed of larger particles than the median volume weighted diameter.

The term "charge control" refers to a propensity of a toner addenda to modify the triboelectric charging properties of the resulting toner.

The term "glass transition temperature" or "Tg" as used herein means the temperature at which a polymer changes from a glassy state to a rubbery state. This temperature (Tg) can be measured by differential thermal analysis as disclosed in "Techniques and Methods of Polymer Evaluation", Vol. 1, Marcel Dekker, Inc., New York, 1966.

The sulfonamides of the invention, which are useful as charge control agents in electrophotographic toners, have the general structure:

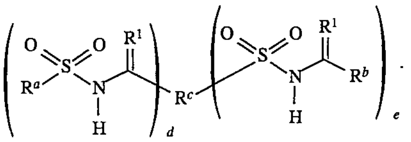

(4)

All designations are defined below. In all structural formulas herein, identical designations, for example the designation: "$R^1$", have the same meaning in all formulas, unless a more narrow definition is specifically indicated.

The sulfonamides of the invention can tautomerize, thus structure (4) could, in many cases, also be represented:

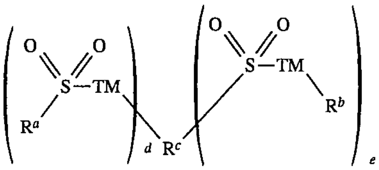

where TM represents

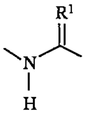 or 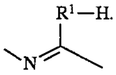

For the sake of brevity, alternate tautomeric forms will not be illustrated herein, however, structural formulas should be understood to be inclusive of alternate tautomers.

Returning now to general formula (4), d and e are each 0, 1, 2, or 3 and the sum of d+e is 2 or 3.

Each $R^a$, $R^b$, and $R^c$ is independently a ring system having a solitary ring or from 2 to 3 fused or linked rings. The ring system is cycloalkyl, aromatic, or heteroaromatic and has from 3 to 34 carbons, counting carbon atoms of any substituent group or groups. In the specific examples described herein, $R^a$, $R^b$, and $R^c$ are phenyl, however, non-phenyl $R^a$, $R^b$, and $R^c$ groups are not currently disfavored.

$R^a$, $R^b$, and $R^c$ groups can be unsubstituted or can have one or more substituents selected from the group: alkyl having from 1 to 20 carbons, $NO_2$, $NH_2$, OH, COOH, cycloalkyl having from 3 to 6 carbons, halo, alkoxy having from 1 to 20 carbons, alkycarbonyloxy having from 2 to 20 carbons and carboalkoxy having from 2 to 20 carbons.

$R^1$ is S, O, NT. T represents H, $R^z$ or -L-$R^z$ where $R^z$ is selected from alkyl having from 1 to 20 carbons, cycloalkyl having from 3 to 18 carbons, and aromatic and heteroaromatic ring systems having a single ring or from 2 to 3 linked or fused rings. The alkyl group or ring system can be unsubstituted or can be substituted with the groups described below in relation to $R^a$ and $R^b$. L is a linking group selected from:

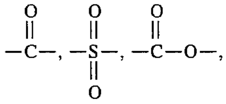

and

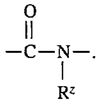

$R^1$=S or O is currently preferred over NT and O is currently preferred over S for use as charge control agents.

Embodiments of the sulfonamides of the invention, which are currently preferred, can be represented by the general structures:

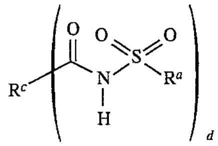

and

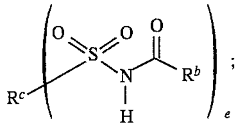

or, alternatively, by the general structures:

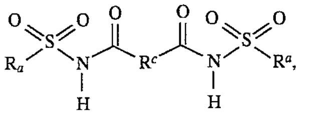

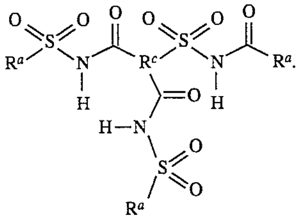

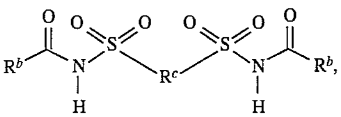

and

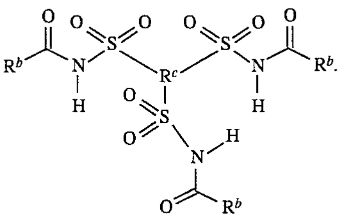

In currently more preferred embodiments of the sulfonamides of the invention, $R^a$, $R^b$ and $R^c$ are each phenyl and at least one of the rings bears a tert-butyl group.

Specific examples of sulfonamide charge control agents of the invention are:

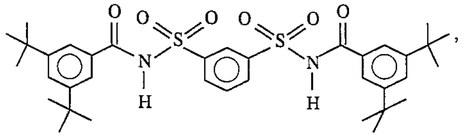

(Z-1)

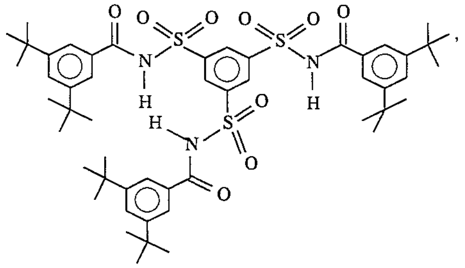

(Z-2)

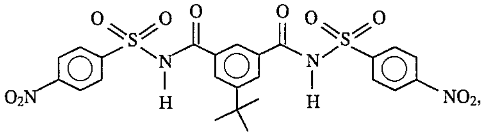

(Z-3)

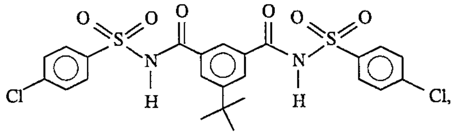

(Z-4)

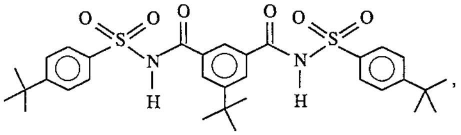

(Z-5)

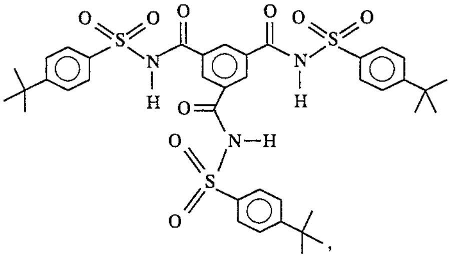

(Z-6)

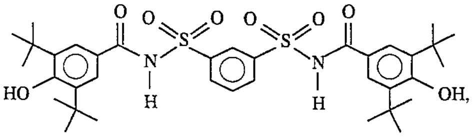

(Z-7)

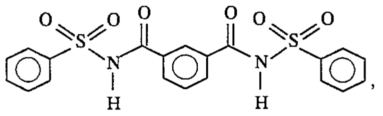

(Z-8)

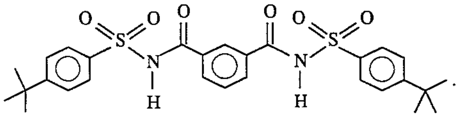

(Z-9)

Other sulfonamides, differing from those claimed herein, are described in U.S. Pat. No. 5,405,727, entitled: "N-(CARBONYL, CARBONIMIDOYL, CARBONOTHIOYL-)SULFONAMIDE CHARGE CONTROL AGENTS AND TONERS AND DEVELOPERS", filed concurrently with this application, by inventors: John C. Wilson, Peter S. Alexandrovich, and Steven M. Bonser, the disclosure of which is hereby incorporated by reference.

The sulfonamides of the invention were prepared in accordance with the following reaction schemes:

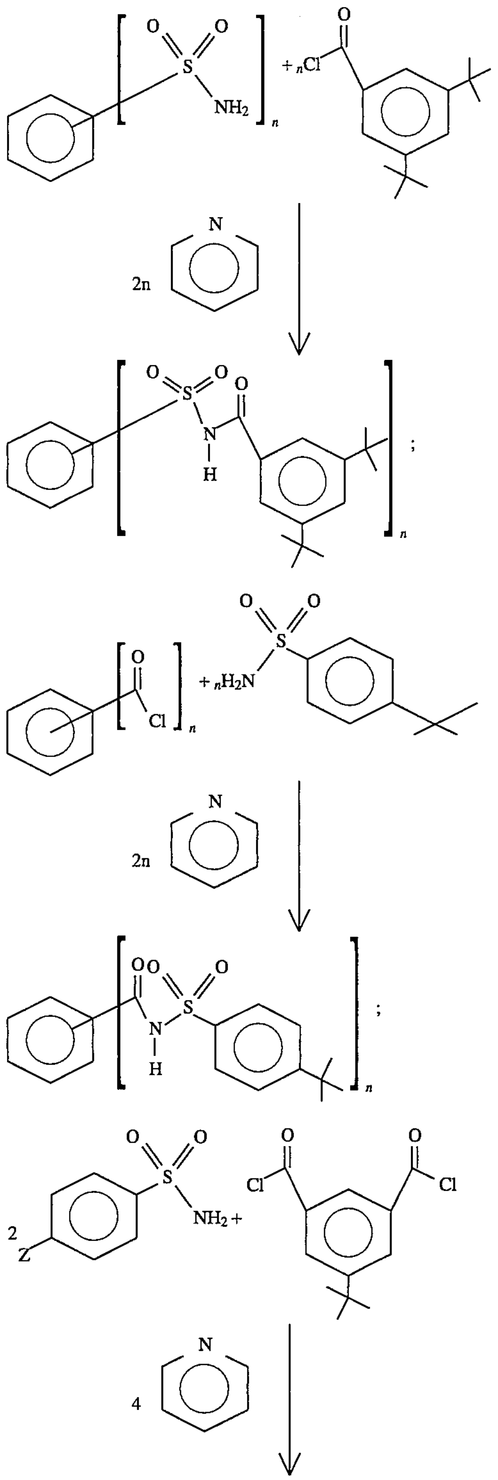

-continued

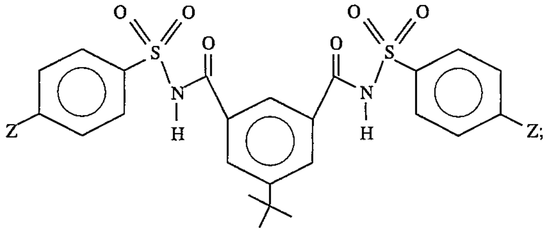

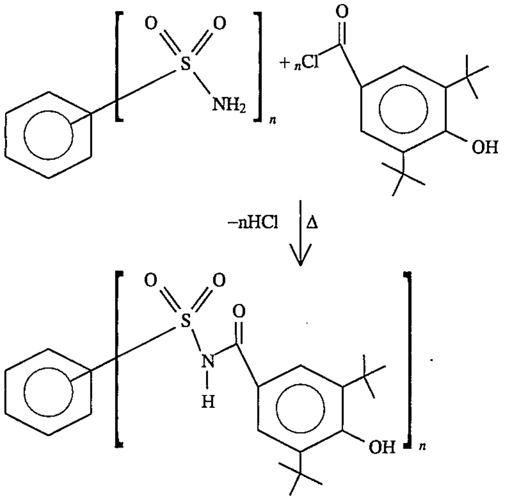

The toner of the invention includes charge control agent of the invention, in an amount effective to modify, and preferably, improve the properties of the toner. It is preferred that a charge control agent improve the charging characteristics of a toner, so the toner quickly charges to a negative value having a relatively large absolute magnitude and then maintains about the same level of charge. Relatively large values of charge per mass that are currently preferred are in the 25–35 microcoloumbs/gram range. Exceeding the upper end of the range can result in low density on copy, and is thus not preferred. The sulfonamides of the invention are negative charge control agents, thus the toners of the invention, it is preferred, achieve and maintain negative charges having relatively large absolute magnitudes.

It is also preferred that a charge control agent improve the charge uniformity of a toner composition, that is, they insure that substantially all of the individual toner particles exhibit a triboelectric charge of the same sign with respect to a given carrier. It is also preferred that toner throw-off be minimized. The term "toner throw-off" refers to the amount of toner powder thrown out of a developer mix as it is mechanically agitated, for example, within a development apparatus. Throw-off can cause unwanted background development and general contamination problems. In some embodiments of the toner of the invention, the charge control agent of the invention is not phase separated. It is preferred that phase separation of the charge control agent used in a toner be minimized (at least in so far as phase separation visible in toner melted onto a glass slide under a microscope at 650 times magnification). It has been determined empirically that such phase separation can correlate with increased clumping of the toner powder, and can lead to irreproducible manufacture of toner. It is also preferred that a charge control agent be colorless, particularly for use in light colored toners. The charge control agents of the invention are colorless. It is also preferred that a charge control agent be metal free and have good thermal stability. The charge contol agents of the invention are metal free and have good thermal stability. Preferred materials described herein are based upon an evaluation in terms of a combination of characteristics rather than any single characteristic.

The properties of the thermoplastic polymers employed as the toner matrix phase in the present invention can vary widely. Typically, and preferably, amorphous toner polymers having a glass transition temperature in the range of about 50° C. to about 120° C. or blends of substantially amorphous polymers with substantially crystalline polymers having a melting temperature in the range of about 65° C. to about 200° C. are utilized in the present invention. Preferably, such polymers have a molecular weight distribution including an insoluble, very high molecular weight fraction and one or more fractions having a number average molecular weight in the range of about 1000 to about 500,000 and a weight average molecular weight in the range of about $2\times10^3$ to about $3\times10^6$. Preferably, the thermoplastic polymers used in the practice of this invention are substantially amorphous. However, as indicated above, mixtures of polymers can be employed, if desired, such as mixtures of substantially amorphous polymers with substantially crystalline polymers.

Polymers useful as binders in the toner of the invention include styrenic/acrylic copolymers. In general, preferred styrenic/acrylic copolymers have a glass transition temperature in the range of about 50° C. to about 100° C. In a particular embodiment of the invention, the resin is a copolymer of styrene and butyl acrylate, crosslinked with divinyl benzene; produced in a suspension or emulsion polymerization process. An initiator and, optionally, a chain transfer agent are used in the synthesis. The ratio of styrene to butyl acrylate is in the range of from 90:10 to 60:40 and the divinyl benzene is used at a level of 3 weight percent or less, preferably, at a level of about 0.1 to 1.0 weight percent.

An optional but preferred component of the toner of the invention is colorant: a pigment or dye. Suitable dyes and pigments are disclosed, for example, in Reissue U.S. Pat. No. 31,072 and in U.S. Pat. Nos. 4,160,644; 4,416,965; 4,414,152; and 2,229,513. One particularly useful colorant for toners to be used in black and white electrostatographic copying machines and printers is carbon black. Colorants are generally employed in the range of from about 1 to about 30 weight percent on a total toner powder weight basis, and preferably in the range of about 2 to about 15 weight percent.

The toner of the invention can also contain other additives of the type used in previous toners, including leveling agents, surfactants, stabilizers, and the like. The total quantity of such additives can vary. A present preference is to employ not more than about 10 weight percent of such additives on a total toner powder composition weight basis.

Dry styrenic/acrylic copolymer toners of this invention can optionally incorporate a small quantity of low surface energy material, as described in U.S. Pat. Nos. 4,517,272 and 4,758,491. Optionally the toner can contain a particulate additive on its surface such as the particulate additive disclosed in U.S. Pat. No. 5,192,637.

The charge control agent is incorporated into the toner. For example, in a dry electrostatographic toner, the charge control agent of the invention can be mixed in any convenient manner, such as blending in the manner described in U.S. Pat. Nos. 4,684,596 and 4,394,430, with an appropriate polymeric binder material and any other desired addenda. The mixture is then gound to desired particle size to form a free-flowing powder of toner particles containing the charge agent.

A preformed mechanical blend of particulate polymer particles, charge control agent, colorants and additives can, alternatively, be roll milled or extruded at a temperature sufficient to melt blend the polymer or mixture of polymers to achieve a uniformly blended composition. The resulting material, after cooling, can be ground and classified, if desired, to achieve a desired toner powder size and size distribution. For a polymer having a $T_g$ in the range of about 50° C. to about 120° C., or a $T_m$ in the range of about 65° C. to about 200° C., a melt blending temperature in the range of about 90° C. to about 240° C. is suitable using a roll mill or extruder. Melt blending times, that is, the exposure period for melt blending at elevated temperature, are in the range of about 1 to about 60 minutes. After melt blending and cooling, the composition can be stored before being ground. Grinding can be carried out by any convenient procedure. For example, the solid composition can be crushed and then ground using, for example, a fluid energy or jet mill, such as described in U.S. Pat. No. 4,089,472. Classification can be accomplished using one or two steps.

In place of blending, the polymer can be dissolved in a solvent in which the charge control agent and other additives are also dissolved or are dispersed. The resulting solution can be spray dried to produce particulate toner powders. Limited coalescence polymer suspension procedures as disclosed in U.S. Pat. No. 4,833,060 are particularly useful for producing small sized, uniform toner particles.

The toner particles have an average diameter between about 0.1 micrometers and about 100 micrometers, and desirably have an average diameter in the range of from about 1.0 micrometers to 30 micrometers for currently used electrostatographic processes. The size of the toner particles is believed to be relatively unimportant from the standpoint of the present invention; rather the exact size and size distribution is influenced by the end use application intended. So far as is now known, the toner particles can be used in all known electrostatographic copying processes.

The developers of the invention include carrier and toner of the invention. Carriers can be conductive, non-conductive, magnetic, or non-magnetic. Carriers are particulate and can be glass beads; crystals of inorganic salts such as aluminum potassium chloride, ammonium chloride, or sodium nitrate; granules of zirconia, silicon, or silica; particles of hard resin such as poly(methyl methacrylate); and particles of elemental metal or alloy or oxide such as iron, steel, nickel, carborundum, cobalt, oxidized iron and mixtures of such materials. Examples of carriers are disclosed in U.S. Pat. Nos. 3,850,663 and 3,970,571. Especially useful in magnetic brush development procedures are iron particles such as porous iron, particles having oxidized surfaces, steel particles, and other "hard" and "soft" ferromagnetic materials such as gamma ferric oxides or ferrites of barium, strontium, lead, magnesium, or aluminum. Such carriers are disclosed in U.S. Pat. Nos. 4,042,518; 4,478,925; and 4,546,060.

Carrier particles can be uncoated or can be coated with a thin layer of a film-forming resin to establish the correct triboelectric relationship and charge level with the toner employed. Examples of suitable resins are the polymers described in U.S. Pat. Nos. 3,547,822; 3,632,512; 3,795,618 and 3,898,170 and Belgian Patent No. 797,132. Other useful resins are fluorocarbons such as polytetrafluoroethylene, poly(vinylidene fluoride), mixtures of these, and copolymers of vinylidene fluoride and tetrafluoroethylene. See for example, U.S. Pat. Nos. 4,545,060; 4,478,925; 4,076,857; and 3,970,571. Polymeric fluorocarbon coatings can aid the developer to meet the electrostatic force requirements mentioned above by shifting the carrier particles to a position in the triboelectric series different from that of the uncoated carrier core material to adjust the degree of triboelectric charging of both the carrier and toner particles. The polymeric fluorocarbon coatings can also reduce the frictional characteristics of the carrier particles in order to improve developer flow properties; reduce the surface hardness of the carrier particles to reduce carrier particle breakage and abrasion on the photoconductor and other components; reduce the tendency of toner particles or other materials to undesirably permanently adhere to carrier particles; and alter electrical resistance of the carrier particles.

In a preferred embodiment of the invention, the carrier is strontium ferrite coated with poly(methyl methacrylate) (PMMA) on a 2 percent weight/weight basis or strontium ferrite coated with dehydrofluorinated and oxidized fluorocarbon as disclosed in U.S. Pat. No. 4,726,994, the specification of which is hereby incorporated by reference herein. The fluorocarbon is coated on a 0.5 percent weight/weight basis. The fluorocarbon carrier is also referred to herein as "modified Kynar".

In a particular embodiment, the developer of the invention contains from about 1 to about 20 percent by weight of toner of the invention and from about 80 to about 99 percent by weight of carrier particles. Usually, carrier particles are larger than toner particles. Conventional carrier particles have a particle size of from about 5 to about 1200 micrometers and are generally from 20 to 200 micrometers.

The toners of the invention are not limited to developers which have carrier and toner, and can be used, without carrier, as single component developer.

The toner and developer of the invention can be used in a variety of ways to develop electrostatic charge patterns or latent images. Such developable charge patterns can be prepared by a number of methods and are then carried by a suitable element. The charge pattern can be carried, for example, on a light sensitive photoconductive element or a non-light-sensitive dielectric surface element, such as an insulator coated conductive sheet. One suitable development technique involves cascading developer across the electrostatic charge pattern. Another technique involves applying toner particles from a magnetic brush. This technique involves the use of magnetically attractable carrier cores. After imagewise deposition of the toner particles the image can be fixed, for example, by heating the toner to cause it to fuse to the substrate carrying the toner. If desired, the unfused image can be transferred to a receiver such as a blank sheet of copy paper and then fused to form a permanent image.

The invention is further illustrated by the following Examples and Comparative Examples. Unless otherwise indicated, all starting materials were commercially obtained. All melting points in the Examples and Comparative Examples are uncorrected. Nuclear magnetic resonance (NMR) spectra were obtained in $CDCl_3$ or dimethylsulfoxide-$d_6$ with a Varian Gemini-200 NMR spectrometer, marketed by Varian Associates, of Palo Alto, Calif. Elemental analyses were performed by combustion techniques, unless otherwise indicated and with the exception that metal analyses were performed by neutron activation techniques. Thermogravimetric analyses were obtained with a Perkin-Elmer 7 series Thermal Analysis System at a heating rate of 10° C./min in air from 75°–400° C. Results are generally only reported here for colorless toners. Both black and blue toners were prepared for many of the sulfonamide charge control agents described herein, and results were in all cases, comparable to results with colorless toners.

In the Examples, a number followed by the letter "A" designates a developer which includes PMMA coated carrier and a letter followed by the letter "B" designates a developer which includes a modified Kynar coated carrier. The same practice is followed in the Comparative Examples, except small letters are used rather than capitals. Structural formulas for the charge control agents of the invention are designated, "Z-(number)". Number designations in the Examples correspond to similar number designations of structural formulas. In Tables 1–4, "Ex" and "Com Ex" are the Example number or Comparative Example number, respectively; "CCA" is the designation of the structural formula of the charge control agent; "m.p." is melting point; "Conc" is the concentration of charge agent in styrene/n-butyl acrylate/divinylbenzene binder resin, expressed in parts per hundred parts of binder resin ("pph"), or weight percent ("wgt %"), as indicated; "P/S" is the visible phase separation at 650X; "2 min" and "10 min" are the charge to mass ratios (Q/m) in microcoloumbs/gram at the indicated times; "bich" indicates simultaneous positive and negative charging; and "T.O. (mg admix)" is throwoff in milligrams.

EXAMPLE 1A–1B

Preparation of Charge Control Agent

Sulfonamide charge control agent having the structural formula:

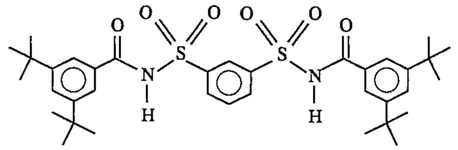

(Z-1)

was prepared as follows. 3,5-Di-t-butylbenzoyl chloride was prepared by reacting 3,5-di-t-butylbenzoic acid and thionyl chloride. A mixture of 23.63 g (0.10 mol) of m-benzenedisulfonamide, 50.56 g (0.20 mol) of 3,5-di-t-butylbenzoyl chloride (previously prepared by reacting 3,5-di-t-butylbenzoic acid and thionyl chloride), and 31.64 grams (0.40 mol) of pyridine was heated on a steam bath for 1.5 hours. The reaction mixture was cooled and a solid precipitated. Dichloromethane (about 2.5 liters) was added resulting in substantial redissolution of the solid. Dilute HCl was added. The reaction mixture was stirred, filtered to remove a small amount of insoluble material, and the water and organic layers were separated. The HCl addition, stirring, and organic and water layer separation steps were repeated twice more. The resulting organic layer was washed with water and separated again, dried over $MgSO_4$ and concentrated, resulting in a viscous, greasy residue. The product was treated with boiling ligroine (bp=35°–60° C.) to crystallize. The solid was collected, substantially dissolved in ethanol, recrystallized, collected, recrystallized from $CH_3CN$, collected, and dried. The resulting white solid was obtained with a yield of 13.3 grams (19.9%). Melting point=291° C. Elemental analysis found C=64.29, H=7.08, N=4.11, S=9.32. This compares to calculated values for $C_{36}H_{48}N_2O_6S_2$ of C=64.64, H=7.23, N=4.19, S=9.59. An NMR spectrum was obtained which agreed with the structure of the expected product.

Preparation of Colorless Toners

A dry blend of 50.0 grams of poly(styrene-co-butylacrylate-co-divinyl benzene) and 0.5 grams of the sulfonamide charge control agent (structural formula Z-1) was added to a heated two-roll compounding mill. The roller surfaces were set to 150° C. The melt was exercised on the mill for 20 minutes, then was removed and cooled. The resulting slab was first coarse ground to 2 mm size on a laboratory mill, then finely pulverized to approximately 12 micrometer size on a Trost TX jet mill. The toner thus prepared had a concentration of charge control agent of 1 part per hundred parts of styrene/n-butyl acrylate/divinylbenzene binder resin. This procedure was repeated, varying the concentration of charge control agent to provide concentrations of 2 and 4 parts per hundred (pph), on the same basis.

Preparation of Black Toners

The same procedures were followed as in the preparation of colorless toner having 1, 2, and 4 pph charge control agent Z-1, with the exception that 3.0 grams of Regal 300 TM carbon black, marketed by Cabot Corp., was added to the dry blend placed in the compounding mill and the slab produced was initially coarse ground to 2 mm size.

Preparation of Blue Toners

The same procedures were followed as in the preparation of colorless toner having 1, 2, and 4 pph charge control agent, with the exception that 5 parts per hundred or copper phthalocyanine blue pigment from BASF Corp., was added to the dry blend placed in the compounding mill and the slab produced was initially coarse ground to 2 mm size.

Preparation of Developers-PMMA coated Carrier

Developer was prepared for each of the toners indicated above, by mixing toner particles prepared as described above at a weight concentration of 12% toner with carrier particles comprising strontium ferrite cores thinly coated (approximately 2 percent by weight) with poly(methyl methacrylate). The volume average particle size of the carrier particles was from about 25 to 35 micrometers.

Preparation of Developers-Modified Kynar Coated Carrier

Developer was prepared for each of the toners indicated above, by mixing toner particles prepared as described above at a weight concentration of 12% toner with carrier particles comprising strontium ferrite cores thinly coated (approximately 0.5 percent weight/weight) with dehydrofluorinated and oxidized fluorocarbon as disclosed in U.S. Pat. No. 4,726,994. The volume average particle size of the carrier particles was from about 25 to 35 micrometers.

Evaluation of Phase Separation

Colorless toners were smear melted onto microscope slides at 180° C. and were examined microscopically at 650X magnification for evidence of phase separation.

Evaluation of Toner Charging

Toner charge was then measured in microcoulombs per gram of toner (μc/g) in a "MECCA" device. Prior to measuring the toner charge, the developer was vigorously shaken or "exercised" to cause triboelectric charging by placing a 4 gram sample of the developer into a plastic vial, capping the vial and shaking the vial on a "wrist-action" robot shaker operated at about 2 Hertz and an overall amplitude of about 11 cm for 2 minutes. Toner charge level after shaking was measured for each sample by placing a 100 milligram sample of the charged developer in a MECCA apparatus and measuring the charge and mass of transferred toner in the MECCA apparatus. This involves placing the 100 milligram sample of the charged developer in a sample dish situated between electrode plates and subjecting it, simultaneously for 30 seconds, to a 60 Hz magnetic field and an electric field of about 2000 volts/cm between the plates. The toner is released from the carrier and is attracted to and collects on the plate having polarity opposite to the toner charge. The total toner charge is measured by an electrometer connected to the plate, and that value is divided by the weight of the toner on the plate to yield the charge per mass of toner (Q/m). The toner charge level (i.e., charge-to-mass ratio) was also taken after exercising the developer for an additional 10 minutes by placing the magnetized developer in a glass bottle on top of a cylindrical roll with rotating magnetic core rotating at 2000 revolutions per minute. The magnetic core had 12 magnetic poles arranged around its periphery, in an alternating north and south fashion. This closely approximates typical actual usage of the developer in an electrostatographic development process. After this additional 10 minute exercising, the toner charge was measured in a MECCA apparatus. Values are reported in Tables 1–2 as Q/m 2 min. and 10 min.

Evaluation of Throw-Off

Throw-off values (T.O.) were determined by taking the 4 gram developer sample at 12% toner concentration that had been exercised for 10 minutes (following the 2 minute exercising), admixing in 6% more toner to provide a final toner concentration of about 18%), followed by 2 minutes more exercise on the wrist action shaker. This developer was then placed on a roll containing a rotating magnetic core, similar to a magnetic brush roll used for electrostatic development. A plexiglass housing contained the assembly, and had a vacuum filter funnel mounted directly over the roll. The weight of toner, in milligrams, collected on a piece of filter paper after one minute of running the magnetic core at 2000 revolutions per minute was reported as the throw-off value.

Results are presented in Tables 1–2.

EXAMPLES 2A, 2B to 8A, 8B

The same procedures were substantially followed as described in Examples 1A, 1B, except that starting materials in the sulfonamide preparation were different. Results are presented in Tables 1–2. The structural formulas of the sulfonamides utilized in these examples are structural formulas Z-2 through Z-8, respectively.

TABLE 1

Developer Using PMMA Coated Carrier

| Ex | CCA | m.p. (°C.) | Conc in pph | P/S | 2 min | 10 min | T.O. (mg admix) |
|---|---|---|---|---|---|---|---|
| 1A | Z-1 | 291 | 1 | oblong chunks 2–12 μm | −25.2 | −35.3 | 0.4 |
| 1A | Z-1 | 291 | 2 | same | −31.4 | −35.9 | 0.3 |
| 1A | Z-1 | 291 | 4 | same | −41.1 | −34.9 | 0.3 |
| 2A | Z-2 | 301 | 1 | no | −19.2 | −30.7 | 1.3 |
| 2A | Z-2 | 301 | 2 | no | −27.3 | −31.6 | 0.8 |
| 2A | Z-2 | 301 | 4 | "grainy" <1 μm | −33.1 | −32.3 | 0.4 |
| 3A | Z-3 | 229–230 | 1 | some rounded flakes 2–10 μm | −21.7 | −17.4 | 4.4 |
| 3A | Z-3 | 229–230 | 2 | some spheres & flakes 2–10 μm | −21.5 | −12.3 | 3.6 |
| 3A | Z-3 | 229–230 | 4 | many spheres 1–15 μm | −20.4 | −10.9 | 4.8 |
| 4A | Z-4 | >250 | 1 | some rounded flakes 1–5 μm | −16.9 | −19.6 | 5.5 |
| 4A | Z-4 | >250 | 2 | same | −22.3 | −16.6 | 3.6 |
| 4A | Z-4 | >250 | 4 | same | −24.1 | −15.3 | 0.9 |
| 5A | Z-5 | >250 | 1 | no | −22.1 | −31.6 | 1.7 |
| 5A | Z-5 | >250 | 2 | no | −26.0 | −30.3 | 1.5 |
| 5A | Z-5 | >250 | 4 | some flakes 1–4 μm | −29.9 | −29.9 | 1.6 |

TABLE 1-continued

Developer Using PMMA Coated Carrier

| Ex | CCA | m.p. (°C.) | Conc in pph | P/S | 2 min | 10 min | T.O. (mg admix) |
|---|---|---|---|---|---|---|---|
| 6A | Z-6 | 205–206 | 1 | no | −21.4 | −23.3 | 2.9 |
| 6A | Z-6 | 205–206 | 2 | no | −25.0 | −22.0 | 2.0 |
| 6A | Z-6 | 205–206 | 4 | some spheres 1–4 μm | −25.5 | −20.8 | 2.6 |
| 7A | Z-7 | 300 decomp | 1 | heavy sep. oblong plates & chunks 2–12 μm | −23.7 | −30.1 | 2.0 |
| 7A | Z-7 | 300 decomp | 2 | same | −29.0 | −25.3 | 2.5 |
| 7A | Z-7 | 300 decomp | 4 | same | −25.5 | −17.9 | 2.0 |
| 8A | Z-8 | 255–257 | 1 | chunks 2–15 μm | −15.7 | −29.2 | 18.3 |
| 8A | Z-8 | 255–257 | 2 | same | −16.2 | −22.9 | 10.3 |
| 8A | Z-8 | 255–257 | 4 | same | −19.4 | −21.8 | 4.4 |

TABLE 2

Developer Using Modified Kynar Carrier

| Ex | CCA | m.p. (°C.) | Conc in pph | P/S | 2 min | 10 min | T.O. (mg admix) |
|---|---|---|---|---|---|---|---|
| 1B | Z-1 | 291 | 1 | oblong chunks 2–12 μm | −20.6 | −52.8 | 0.3 |
| 1B | Z-1 | 291 | 2 | same | −31.3 | −53.9 | 0.3 |
| 1B | Z-1 | 291 | 4 | same | −36.2 | −51.0 | 0.5 |
| 2B | Z-2 | 301 | 1 | no | −14.6 | −36.7 | 0.4 |
| 2B | Z-2 | 301 | 2 | no | −20.2 | −33.1 | 0.8 |
| 2B | Z-2 | 301 | 4 | "grainy" <1 μm | −20.6 | −33.4 | 0.9 |
| 3B | Z-3 | 229–230 | 1 | some rounded flakes 2–10 μm | −17.8 | −21.6 | 1.0 |
| 3B | Z-3 | 229–230 | 2 | some spheres & flakes 2–10 μm | −21.2 | −6.0 | 5.6 |
| 3B | Z-3 | 229–230 | 4 | many spheres 1–15 μm | −19.6 | −2.7 | 183.1 |
| 4B | Z-4 | >250 | 1 | some rounded flakes 1–5 μm | −13.1 | −28.7 | 0.7 |
| 4B | Z-4 | >250 | 2 | same | −14.3 | −16.3 | 1.1 |
| 4B | Z-4 | >250 | 4 | same | −17.8 | −9.8 | 2.4 |
| 5B | Z-5 | >250 | 1 | no | −17.0 | −54.3 | 0.3 |
| 5B | Z-5 | >250 | 2 | no | −19.5 | −49.0 | 0.2 |
| 5B | Z-5 | >250 | 4 | some flakes 1–4 μm | −24.3 | −41.1 | 0.0 |
| 6B | Z-6 | 205–206 | 1 | no | −16.5 | −39.0 | 0.4 |
| 6B | Z-6 | 205–206 | 2 | no | −17.8 | −21.5 | 0.8 |
| 6B | Z-6 | 205–206 | 4 | some spheres 1–4 μm | −19.4 | −18.1 | 1.7 |

COMPARATIVE EXAMPLES

COMPARATIVE EXAMPLES 1a, 1b

Toners and developers were prepared and evaluated in the same manner as in Examples 1A–1B, with the exception that no charge control agent was used.

COMPARATIVE EXAMPLES 2a, 2b

Saccharin (ortho-benzoic sulfimide), which has the structural formula:

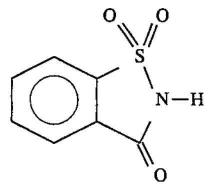

was purchased from Aldrich Chemical Company of Milwaukee, Wis. Toners and developers were prepared and evaluated in the same manner as in Examples 1A–1B, with the exception that saccharin was used in place of sulfonamide charge control agent. Results are presented in Tables 18–19.

COMPARATIVE EXAMPLES 3a, 3b 1-(2-Hydroxyphenyl)-3-(3,5-di-t-butylphenyl)- 1,3-propanedione, which has the structural formula:

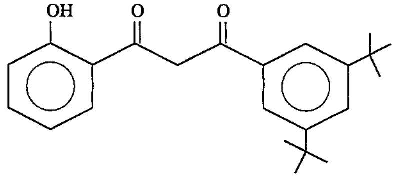

was prepared utilizing the following reaction scheme:

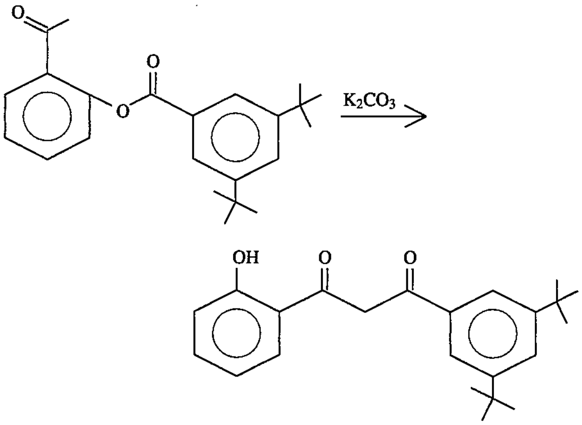

A mixture of 2'-(3,5-di-t-butylbenzoyloxy)acetophenone (55.0 g, 0.156 mol), $K_2CO_3$ (165 g), and toluene (550 ml) was prepared and heated on a steam bath with stirring. Within about two hours, a considerable amount of yellow solid had formed. The heating was continued for a total of about 21 hours. The reaction mixture was filtered hot. The solid collected was washed with ligroine (bp=35°–60° C.), dried, slurried in water, collected, and washed with a 1:1 mixture of acetic acid and water. The solid became taffy-like. The aqueous phase was decanted and the product was washed with water, and recrystallized in about 300 ml of ethanol. Solid in the form of yellow needles was collected and dried. The solid was then dissolved in dichloromethane and the solution was filtered to remove water soluble salts. The filtrate was washed with water, dried over $MgSO_4$ and concentrated. Oily residue was obtained which crystallized on cooling. This solid was recrystallized from 50 ml of ethanol. The precipitate was collected and dried. Yield was 20.3 grams (36.9%). Melting point was 92°–94° C. (Began to melt at 75° C. then solidified. Completely melted at 92°–94° C.). Elemental analysis found C=78.37, H=7.93. This compares to calculated values for $C_{22}H_{28}O_3$ of C=78.38, H=8.01. An NMR spectrum, in deuterated chloroform, was obtained which agreed with the structure of the expected product.

Toners and developers were prepared and evaluated in the same manner as in Examples 1A, 1B, with the exception that 1-(2-hydroxyphenyl)-3-(3,5-di-t-butylphenyl)- 1,3-propanedione was used in place of sulfonamide charge control agent. Results are reported in Tables 3–4.

COMPARATIVE EXAMPLES 4a, 4b

Bis{1-(2-hydroxyphenyl)-3-(4-t-butylphenyl)- 1,3-propanedionato}zinc, which has the structural formula:

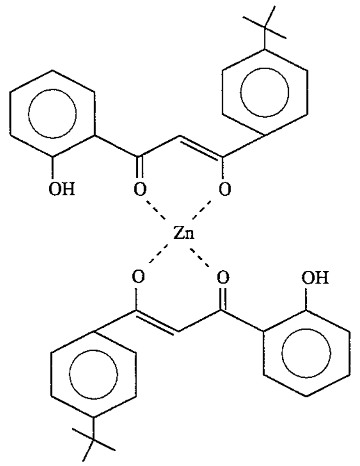

was prepared utilizing the following reaction scheme:

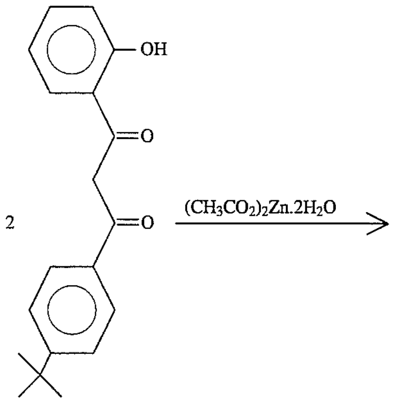

-continued

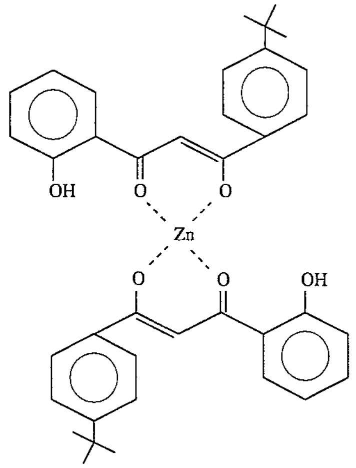

1-(2-hydroxyphenyl)-3-(4-t-butylphenyl)-1,3-propanedione was prepared by the procedure described in Comparative Examples 4, with the exception that 2'-( 4-t-butylbenzoyloxy)acetophenone was substituted for 2'-( 3,5-di-t-butylbenzoyloxy)acetophenone.

A solution of 1-(2-hydroxyphenyl)-3-(4-t-butylphenyl)-1,3-propanedione (2.96 g, 0.10 mol) in methanol (50 ml) was prepared with heating. To this solution, was added a solution of zinc acetate dihydrate (1.11 g, 5 mmol) in methanol (10 ml), which had been preheated. The resulting reaction mixture was heated on a steam bath for 15 minutes. A solid crystalline precipitate that formed was filtered hot, washed with methanol and dried. Yield was 1.17 grams. Melting point was 126°–128° C. (The melt recrystallized to provide a product with a melting point in excess of 250° C.). Elemental analysis found C=69.19, H=5.68, Zn=11.6. This compares to calculated values for $C_{38}H_{38}O_6Zn$ of C=69.57, H=5.84, Zn=9.97. An NMR spectrum, in deuterated chloroform, was obtained which agreed with the structure of the expected product.

Toners and developers were prepared and evaluated in the same manner as in Examples 1A, 1B, with the exception that Bis{1-(2-hydroxyphenyl)-3-(4-t-butylphenyl)- 1,3-propanedionato}zinc was used in place of sulfonamide charge control agent. Results are reported in Tables 3–4.

COMPARATIVE EXAMPLES 5a, 5b 3,5-Di-t-butyl-4-hydroxybenzenesulfonamide has the structural formula

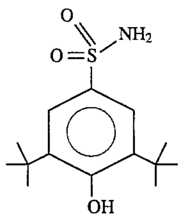

and was prepared as follows.

3,5-Di-t-butyl-4-hydroxybenzenesulfonyl chloride was prepared according to the procedure of U.S. Pat. No. 5,157,156 to Giodana et al.

A solution of 149.5 grams (0.49 mol) of 3,5-di-t-butyl-4-hydroxybenzenesulfonyl chloride in 1700 ml of methylene chloride was treated with ammonia for 35 minutes. The milky organic layer was concentrated to dryness and the solid residue was taken up in acetone, filtered and concentrated. The residue was taken up in ether, washed with water and dried over $MgSO_4$ and concentrated. The residue was recrystallized from 600 ml of isopropanol to give 99.0 grams of product (70.8% of theory). Melting point=166°–168° C. Elemental analysis found C=58.55, H=8.07, N=4.98, S=10.93. This compares to calculated values for $C_{14}H_{23}NO_3S$ of C=58.92, H=8.12, N=4.91, S=11.23. An NMR spectrum was obtained which agreed with the structure of the expected product.

Toners and developers were prepared and evaluated in the same manner as in Examples 1A, 1B, with the exception of the different charge control agent. Results are reported in Tables 3–4.

TABLE 3

Developer Using PMMA Coated Carrier

| Com Ex | m.p. (°C.) | Conc wgt % | P/S | 2 min | 10 min | T.O. (mg admix) |
|---|---|---|---|---|---|---|
| 1a | — | — | — | −7.8 | −49.8 | 4.7 |
| 2a | 228 | 1 | N | −16.4 | −28.1 | 24.6 |
| 2a | 228 | 2 | N | −18.8 | −30.4 | 13.5 |
| 2a | 228 | 4 | N | −28.1 | −36.6 | 5.0 |
| 3a | 92–94 | 1 | N | −10.8 | −37.3 | 1.8 |
| 3a | 92–94 | 2 | N | −11.0 | −35.4 | 2.1 |
| 3a | 92–94 | 4 | N | −11.7 | −34.1 | 2.8 |
| 4a | 126–128 | 1 | Y | −15.5 | −35.1 | 1.5 |
| 4a | 126–128 | 2 | Y | −15.2 | −34.1 | 3.9 |
| 4a | 126–128 | 4 | Y | −15.2 | −33.7 | 2.8 |
| 5a | 166–168 | 1 | N | −16.7 | −44.5 | 0.8 |
| 5a | 166–168 | 2 | N | −17.4 | −47.1 | 3.1 |
| 5a | 166–168 | 4 | N | −17.8 | −48.9 | 2.2 |

TABLE 4

Developer Using Modified Kynar Carrier

| Com Ex | m.p. (°C.) | Conc wgt % | P/S | 2 min | 10 min | T.O. (mg admix) |
|---|---|---|---|---|---|---|
| 1b | — | — | — | −7.3 | −73.2 | 0.1 |
| 2b | 228 | 1 | N | bich | −29.7 | 11.2 |
| 2b | 228 | 2 | N | bich | −4.7 | 126.3 |
| 2b | 228 | 4 | N | bich | −1.8 | 217.8 |
| 3b | 92–94 | 1 | N | −2.2 | −53.0 | 0.3 |
| 3b | 92–94 | 2 | N | −1.7 | −43.6 | 0.0 |
| 3b | 92–94 | 4 | N | −1.9 | −40.2 | 0.4 |
| 4b | 126–128 | 1 | Y | −7.3 | −46.7 | 0.3 |
| 4b | 126–128 | 2 | Y | −3.6 | −36.9 | 0.6 |
| 4b | 126–128 | 4 | Y | −4.4 | −38.7 | 0.5 |
| 5ba | 166–168 | 1 | N | −13.7 | −73.2 | 0.1 |
| 5b | 166–168 | 2 | N | −12.5 | −65.3 | 0.2 |
| 5b | 166–168 | 4 | N | −10.4 | −70.6 | 0.2 |

While specific embodiments of the invention have been shown and described herein for purposes of illustration, the protection afforded by any patent which may issue upon this application is not strictly limited to a disclosed embodiment; but rather extends to all modifications and arrangements which fall fairly within the scope of the claims which are appended hereto.

What is claimed is:

1. A sulfonamide having the general structure:

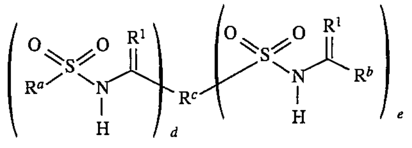

wherein each $R^1$ is O;

$R^a$, $R^b$, and $R^c$ are substituted or unsubstituted phenyl and at least one of $R^a$, $R^b$, and $R^c$ is tert-alkylated;

d is an integer from 0 to 3;

e is an integer from 0 to 3; and the sum of d+e is 2 or 3.

2. A sulfonamide according to claim 1 wherein e is 0.

3. A sulfonamide according to claim 1 having the general structure:

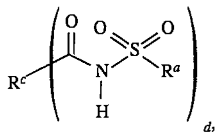

wherein $R^a$ and $R^c$ are unsubstituted or are substituted by moieties selected from the group consisting of alkyl having from 1 to 20 carbons, $NO_2$, $NH_2$, OH, COOH, cycloalkyl having from 3 to 6 carbons, halo, alkycarbonyloxy having from 2 to 20 carbons and carboalkoxy having from 2 to 20 carbons, and alkoxy having from 1 to 20 carbons.

4. A sulfonamide according to claim 1 having the general structure:

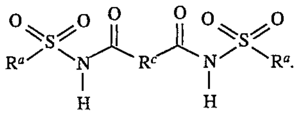

5. A sulfonamide according to claim 1 having the general structure:

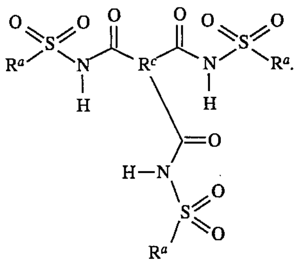

6. A sulfonamide according to claim 1 wherein d is 0.

7. A sulfonamide according to claim 1 having the general structure:

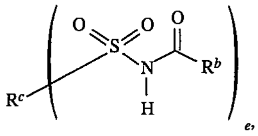

wherein $R^b$ and $R^c$ are unsubstituted or are substituted by moieties selected from the group consisting of alkyl having from 1 to 20 carbons, $NO_2$, $NH_2$, OH, COOH, cycloalkyl having from 3 to 6 carbons, halo, alkycarbonyloxy having from 2 to 20 carbons and carboalkoxy having from 2 to 20 carbons, and alkoxy having from 1 to 20 carbons.

8. A sulfonamide according to claim 1 having the general structure:

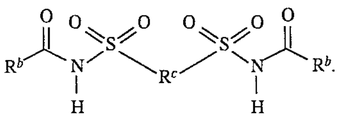

9. A sulfonamide according to claim 1 having the general structure:

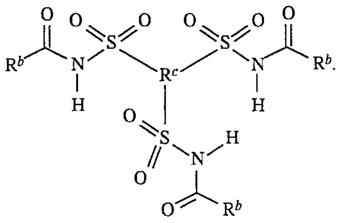

10. A sulfonamide according to claim 1 wherein said $R^a$, $R^b$, and $R^c$ are, independently, unsubstituted or are substituted by moieties selected from the group consisting of alkyl having from 1 to 20 carbons, $NO_2$, $NH_2$, OH, COOH, cycloalkyl having from 3 to 6 carbons, halo, alkycarbonyloxy having from 2 to 20 carbons and carboalkoxy having from 2 to 20 carbons, and alkoxy having from 1 to 20 carbons.

11. A sulfonamide according to claim 1 having the general formula:

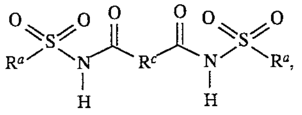

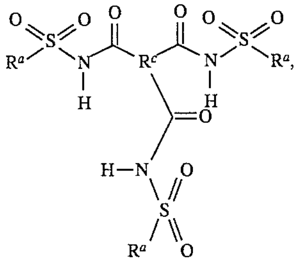

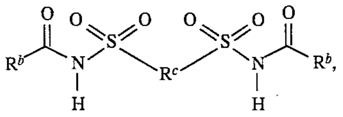

or

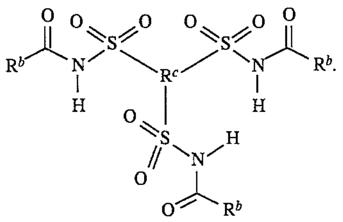

12. A sulfonamide according to claim 1 having the structure:

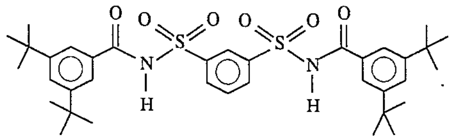

13. A sulfonamide according to claim 1 having the structure:

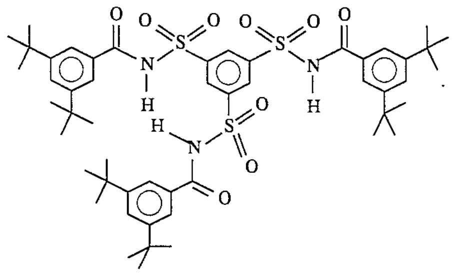

14. A sulfonamide according to claim 1 having the structure:

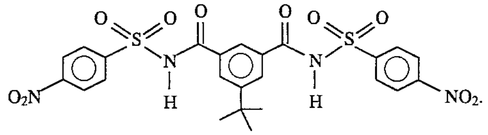

15. A sulfonamide according to claim 1 having the structure:

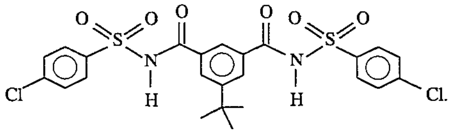

16. A sulfonamide according to claim 1 having the structure:

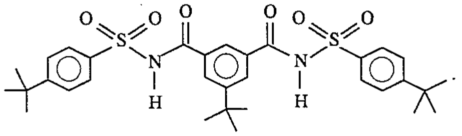

17. A sulfonamide according to claim 1 having the structure:

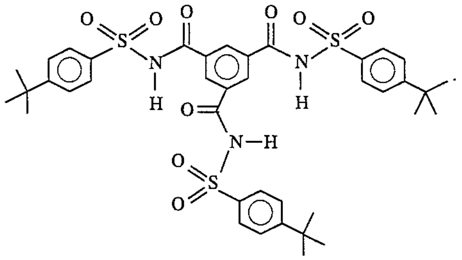

18. A sulfonamide according to claim 1 having the structure:
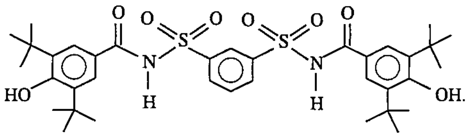
19. A sulfonamide according to claim 1 having the structure:
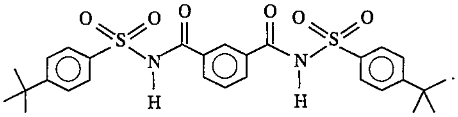
* * * * *